United States Patent [19]

Child

[11] 4,385,633
[45] * May 31, 1983

[54] TEAT DILATOR

[75] Inventor: Francis W. Child, Eagle Bend, Minn.

[73] Assignee: Child Laboratories Inc., Cody, Wyo.

[*] Notice: The portion of the term of this patent subsequent to Aug. 4, 1998, has been disclaimed.

[21] Appl. No.: 277,278

[22] Filed: Jun. 25, 1981

Related U.S. Application Data

[63] Continuation-in-part of Ser. No. 185,179, Sep. 8, 1980, Pat. No. 4,346,714, which is a continuation-in-part of Ser. No. 55,994, Jul. 9, 1979, Pat. No. 4,281,658.

[51] Int. Cl.³ .............................................. A61M 29/00
[52] U.S. Cl. .................................... 604/104; 604/246
[58] Field of Search ............... 128/341, 343, 348, 350, 128/349, 130, 274; 119/71, 14.19, 14.2, 14.21; 222/218, 494, 528; 251/342

[56] References Cited

U.S. PATENT DOCUMENTS

| | | |
|---|---|---|
| 15,192 | 6/1856 | Peale . |
| 119,932 | 2/1871 | Hewitt ............................. 119/14.19 |
| 274,447 | 3/1883 | Kennish . |
| 1,045,326 | 11/1912 | Ruflin ................................ 128/349 |
| 1,116,376 | 11/1914 | Browning ......................... 119/14.22 |
| 1,242,314 | 10/1917 | Bean ............................... 128/349 R |
| 1,593,832 | 7/1926 | Larson .............................. 128/242 |
| 1,688,795 | 10/1928 | Aas .................................. 128/348 R |
| 1,995,051 | 3/1935 | Benson ........................... 119/14.21 |
| 2,450,217 | 9/1948 | Alcorn .............................. 128/350 |
| 2,687,731 | 8/1954 | Iarussi ............................... 128/349 |
| 2,704,076 | 3/1955 | Larson .............................. 128/348 |
| 2,827,054 | 3/1958 | Towne ............................... 128/341 |
| 3,030,960 | 4/1962 | Turner .............................. 128/348 |
| 3,071,139 | 1/1963 | Nicholson ......................... 128/350 |
| 3,703,898 | 11/1972 | Zackheim ...................... 128/341 X |
| 3,821,956 | 7/1974 | Gordhamer ....................... 128/343 |
| 3,881,448 | 5/1975 | Hallstrom ...................... 119/14.19 |
| 4,281,658 | 8/1981 | Child ................................. 128/348 |

OTHER PUBLICATIONS

Honda, Service Repair Handbook, All Civic Models, 1973–1974, Clymer Publications.

*Primary Examiner*—Stephen C. Pellegrino
*Attorney, Agent, or Firm*—Burd, Bartz & Gutenkauf

[57] ABSTRACT

A dilator for a teat of a dairy cow operates to facilitate the flow of fluid from the teat. The dilator has a body having a passage adapted to be positioned in communication with a duct of the teat. An elongated tubular member extends from the body into the duct. The tubular member has a passage allowing the flow of fluid through the dilator. A one-way valve mounted on the body allows the flow of fluid out of the dilator and restricts the entrance of external foreign substances back into the passage and duct of the teat. The valve has flexible side walls terminating in normally closed lips. A slit mouth is located between the lips. The slit mouth can be opened to facilitate the dispensing of medicinal compounds into the teat and udder of the mammal. An inserter having a rod extended through the one-way valve and tubular member is used to place the dilator in the teat duct and duct outlet, with the one-way valve located at the terminal end of the teat.

21 Claims, 21 Drawing Figures

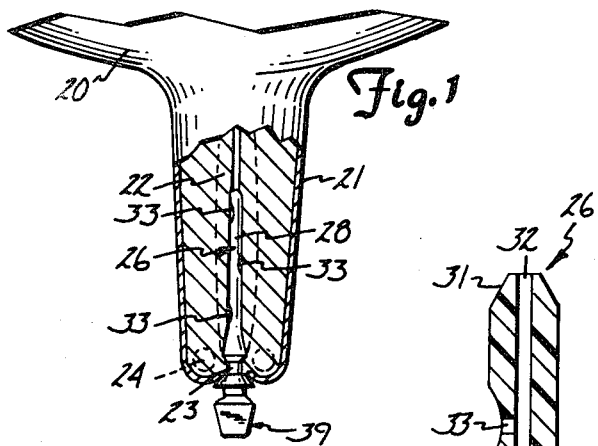
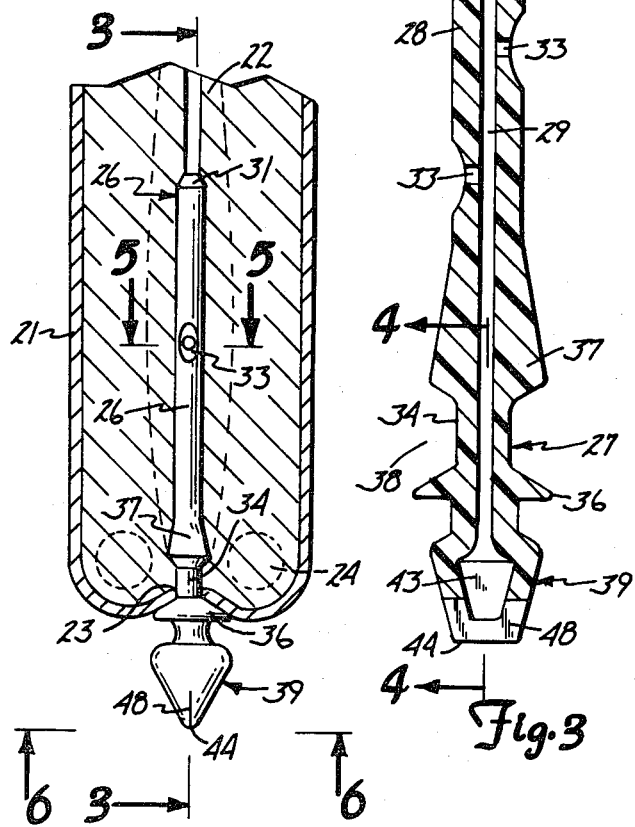
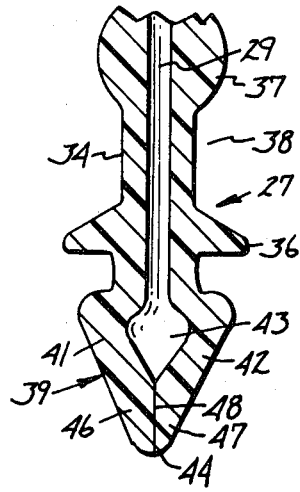
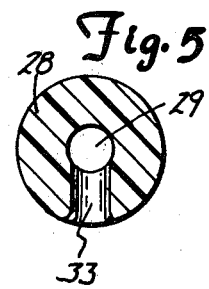
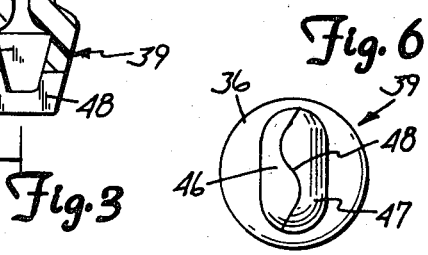

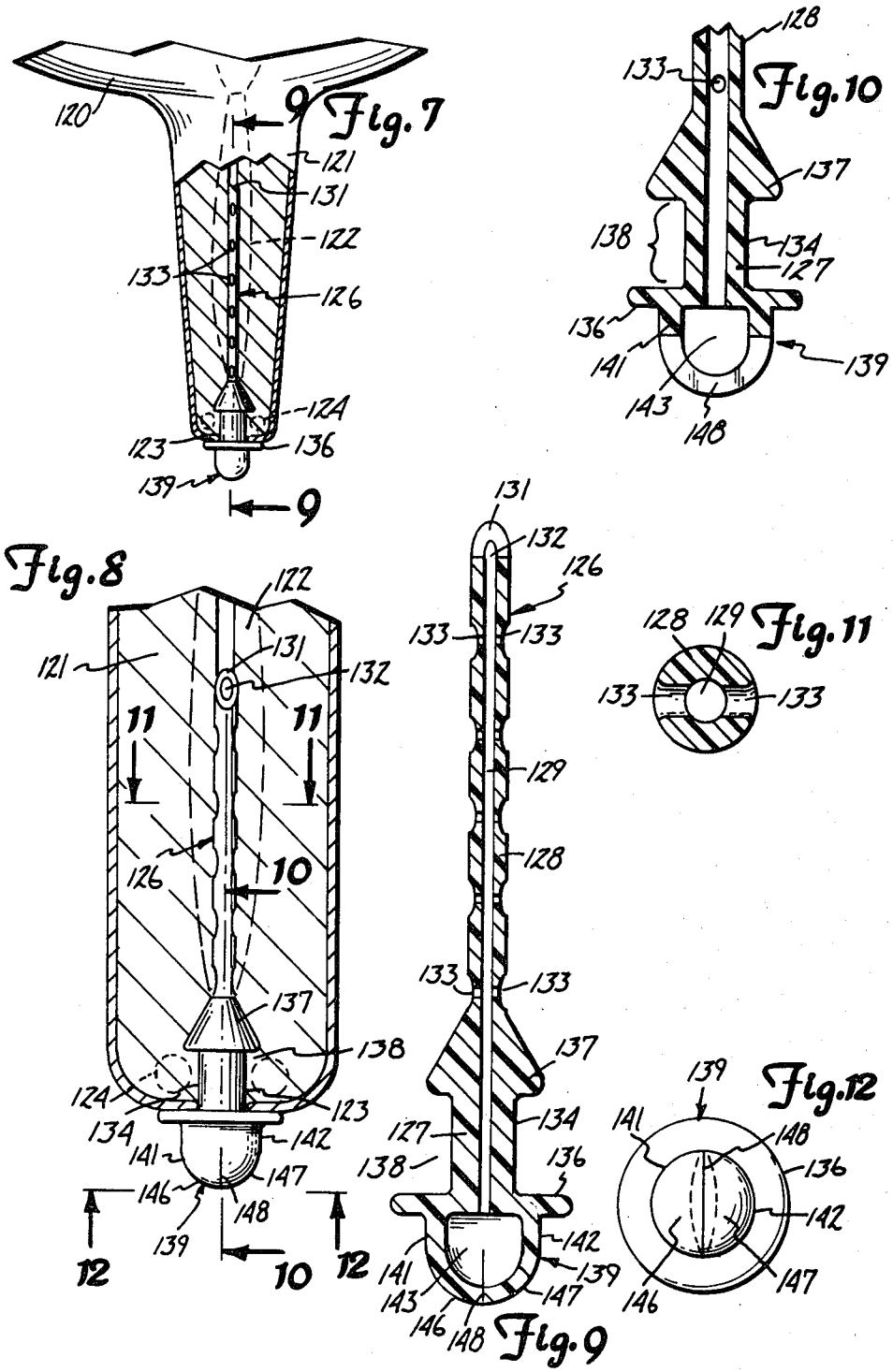

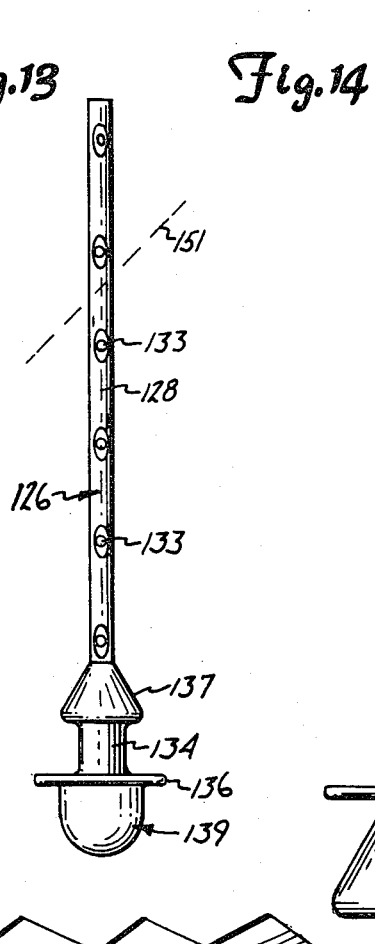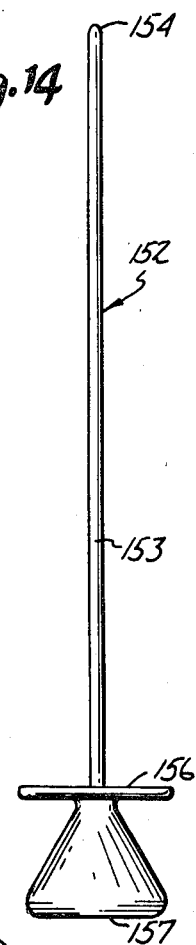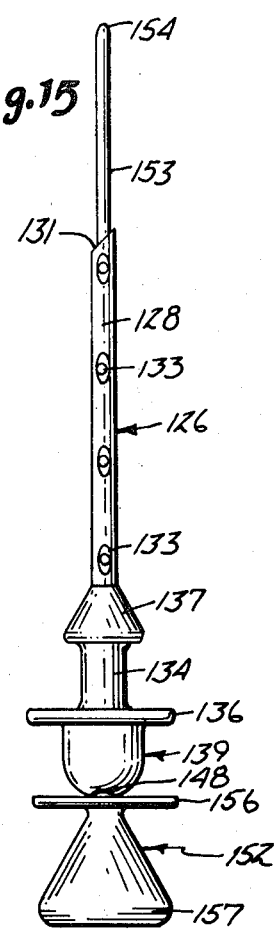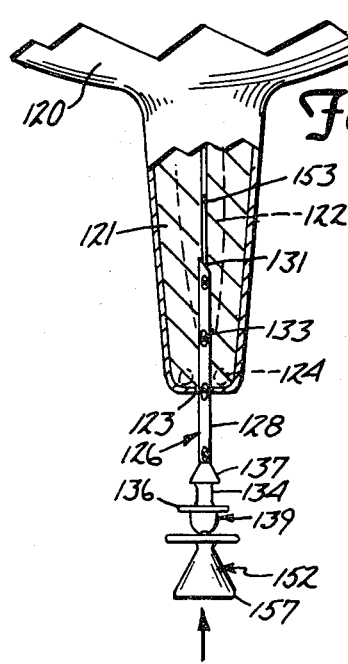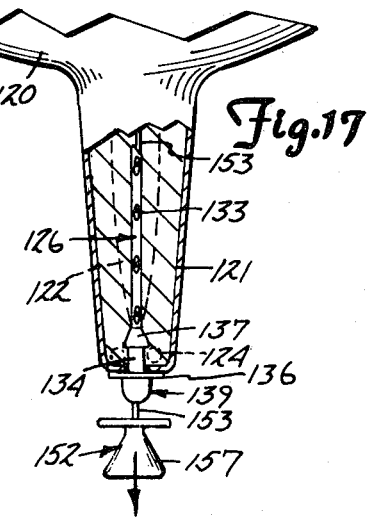

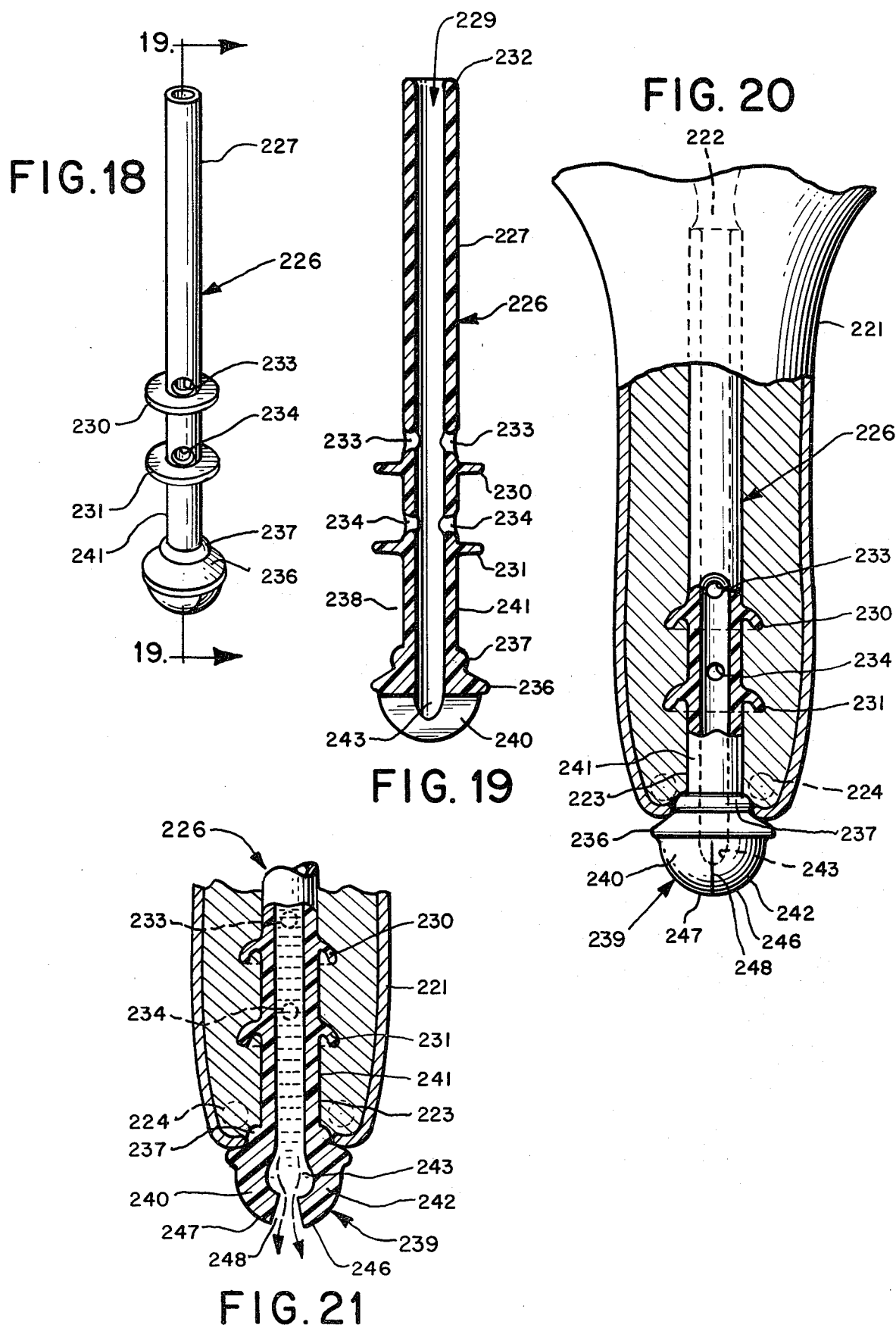

TEAT DILATOR

CROSS REFERENCE TO RELATED APPLICATIONS

This Application is a continuation-in-part of U.S. patent application Ser. No. 185,179, filed Sept. 8, 1980. U.S. patent application Ser. No. 185,179, filed Sept. 8, 1980 now U.S. Pat. No. 4,346,714 granted Aug. 31, 1982, is a continuation-in-part of U.S. patent application Ser. No. 055,994, filed July 9, 1979, now U.S. Pat. No. 4,281,658 granted Aug. 4, 1981.

SUMMARY OF THE INVENTION

The invention is an apparatus adapted to be inserted into a passage in a body to facilitate the movement of fluid through the passage in one direction and restrict or limit the flow of fluid and external substances back into the passage. The apparatus has first means having a passage for carrying fluid adapted to be located in a body passage. A one-way valve means associated with the first means allows fluid to flow out of the passage of the first means and restrict the movement of foreign material located externally of the body back into the passage and thereby eliminate the contamination of the body.

More particularly, the apparatus is a teat dilator for use to control the flow of fluid, such as milk, out of the teat of a bovine animal or a caprine animal and restrict reverse flow of fluids and materials back into the teat to minimize contamination of the teat and udder. The dilator has a tubular body surrounding a longitudinal passage. The body is connected to an elongated tubular member having a longitudinal passage and a plurality of side holes open to the passage to facilitate the flow of fluid through the passage. The elongated tubular member is a flexible tubular plastic that is compatible with the body tissues and fluids. A one-way valve means is attached to one end of the tubular member to control the flow of fluids from the tubular member and restrict or prevent the entrance of foreign substances, both liquid and solid, bacteria, viruses, and the like from moving through the one-way valve and into the teat canal to control mastitis in the teat and udder.

At least one annular flange and annular shoulder joined to the tubular member above the one-way valve cooperate with the sphincter muscle of the teat to firmly retain the dilator in the teat and minimize the entrance of foreign substances into the teat canal. The one-way valve means has flexible side walls that terminate in normally closed lips. A slit between the lips forms a slit mouth that is normally closed. The flexible side walls move in response to pressure of fluid in the teat canal to an open position and thereby permit the flow of the fluid through the one-way valve. The one-way valve is preferably integral with the annular flange to locate the valve adjacent the end of the teat.

The invention includes a method of inserting a dilator having an elongated flexible tubular member having a longitudinal passage and a one-way valve into a teat of a bovine animal, as a dairy cow. The teat of a dairy cow has a longitudinal duct and a duct outlet in the terminal end thereof. The forward end of the tubular member is initially cut off to shorten the tubular member to a length that is shorter than the length of the teat. When the dilator is used with a long teat, the tubular member is not shortened. The dilator is mounted on an elongated inserter. The inserter has a relatively rigid rod that extends through the one-way valve and tubular member. The dilator and inserter are moved through the duct outlet, locating the tubular member in the teat duct. The sphincter muscle of the teat located between the flange and shoulder of the body of the dilator holds the dilator in the inserted position in the teat. The inserter is removed from the dilator by withdrawing the rod from the tubular member and one-way valve. The one-way valve returns to the closed position as soon as the rod separates from the resilient lips of the valve side walls.

IN THE DRAWINGS

FIG. 1 is an elevational view partly in section of a teat and udder of a mammal with a teat dilator embodying the invention inserted in the milk duct of the teat;

FIG. 2 is an enlarged sectional view of a teat with the teat dilator inserted into the milk duct of the teat;

FIG. 3 is an enlarged sectional view taken along the line 3—3 of FIG. 2;

FIG. 4 is an enlarged sectional view taken along the line 4—4 of FIG. 3;

FIG. 5 is an enlarged sectional view taken along the line 5—5 of FIG. 2;

FIG. 6 is an end view of the one-way valve unit viewing along line 6—6 of FIG. 2 in the direction of the arrows;

FIG. 7 is a side elevational view of a modified teat dilator of the present invention inserted in the teat of a bovine animal;

FIG. 8 is an enlarged side elevational view of the dilator of FIG. 7 inserted into the milk duct of the teat;

FIG. 9 is an enlarged sectional view taken along the line 9—9 of FIG. 7;

FIG. 10 is an enlarged sectional view taken along the line 10—10 of FIG. 8;

FIG. 11 is an enlarged sectional view taken along the line 11—11 of FIG. 8;

FIG. 12 is an end view of the one-way valve of the dilator of FIG. 8 viewing along the line 12—12 in the direction of the arrows;

FIG. 13 is an enlarged elevational view of the dilator of FIG. 7;

FIG. 14 is a side elevational view of the inserter used to place the dilator in the milk duct of the teat of a bovine animal;

FIG. 15 is a side elevational view of the inserter in assembled relation with the teat dilator prior to the insertion of the dilator into the milk duct;

FIG. 16 is a side elevational view of the inserter and dilator and teat partly sectioned showing the insertion of the dilator into the milk duct of a teat with the inserter;

FIG. 17 is a view similar to FIG. 16 showing the dilator in the inserted position, with the inserter being removed from the dilator and teat.

FIG. 18 is a side perspective view of a modified teat dilator of the present invention;

FIG. 19 is an enlarged sectional view taken along line 19—19 of FIG. 18;

FIG. 20 is an enlarged, partially sectioned side view of the teat dilator of FIG. 18 inserted into the teat of a bovine animal; and FIG. 21 is a further enlarged view of the lower section of the teat dilator of FIG. 18, with its one-way valve in the open position typical during passage of fluid therethrough.

DESCRIPTION OF PREFERRED EMBODIMENTS

Referring to FIG. 1, there is shown a portion of the mammary system of a mammal having an udder 20 carrying an elongated downwardly directed teat 21. Teat 21 is an enlarged muscular member having a duct or cistern 22 accommodating fluid, as milk, extended from milk cisterns of udder 20 to a normally closed outlet or streak canal 23 at the terminal end of the teat. An annular sphincter muscle 24 maintains outlet 23 in a contracted closed condition. Teat 21 hereinafter described is one of the teats of a bovine animal, as a milk cow. The dilator 26 of the invention is used to control mastitis in the teat and udder of dairy cattle.

Dilator 26 of the invention can be used with teats of other mammals, as caprine animals. The use of dilator 26 is not limited to the use of teats of mammals. The dilator can be inerted into body and tissue ducts and cavities to control the flow of fluid from the ducts and cavities and restrict the entrance of foreign materials into the ducts and cavities. The one-way valve, when closed, functions as a barrier which prevents foreign materials from freely moving into the duct or cavity.

The dilator indicated generally at 26 is shown in FIGS. 1 and 2 in the inserted position in milk duct 22. Dilator 26 has an elongated cylindrical member or body indicated generally at 27. A tubular finger or tubular member 28 is joined to and extends upwardly from body 27. Tubular member 28 and body 27 have a continuous longitudinal passage 29 for carrying the fluid and milk. The upper end of tubular member 28 terminates in a semi-spherical or rounded forward tip 31 to facilitate the insertion and movement of tubular member 28 through duct outlet 23 up into the milk duct 22 of teat 21. Tip 31 surrounds an inlet opening 32 of passage 29. The sides of tubular member 28 have a plurality of holes 33 open to passage 29 to facilitate the flow of fluid from milk duct 22 into passage 29. The outer portions of holes 33 are enlarged so that fluid in duct 22 is free to flow through holes 33 into passage 29.

Body 27 has a cylindrical neck 34 joined to an enlarged flange or head 36. A curved outwardly directed shoulder 37 is joined to and surrounds the inner or lower end of tubular member 28. Shoulder 37 has an upwardly and inwardly tapered outer surface which facilitates insertion of shoulder 37 through duct outlet 23. Shoulder 37 is longitudinally spaced from flange 36 and forms with neck 34 an annular groove 38 to accomodate the tissue and sphincter muscle 24 surrounding the duct outlet 23. When tubular member 28 of dilator 26 is fully inserted into the teat duct 22, sphincter muscle 24 and surrounding tissue are located in groove 38 to retain dilator 26 in the inserted position in teat 22.

A one-way valve indicated generally at 39 is integral with the lower end of body 27. Valve 39, as shown in FIG. 4, has a pair of downwardly converging flexible side walls 41 and 42 surrounding a chamber 43. Chamber 43 is open to the bottom of passage 29. Side walls 41 and 42 have generally U-shaped configurations with tapering outside surfaces and tapering ends converging to a generally flat end or nose 44. The lower end of side walls 41 and 42 has flexible lips 46 and 47 with normally engaging surfaces forming a mouth 48. As shown in FIG. 6, mouth 48 has a generally S-curved shape which allows the mouth to be opened in response to the pressure of fluid in passage 29 and chamber 43. For example, when the side walls of teat 21 are compressed, such as in a milking operation, the increase of the pressure of the fluid in duct 22 will cause the flexible side walls 41 and 42 and lips 46 and 47 to move away from each other or open to allow the fluid to flow through the dilator passage 29 and one-way valve 39. Mouth 48 can be a straight line or slit. Other shapes, such as a Z-shape, can be used for the mouth 39. Side walls 41 and 42 and lips 46 and 47 have elastic strength and memory so that when the pressure of the fluid in teat duct 22 is relieved, the one-way valve 39 will automatically close. Valve 39 remains closed under the normal pressure of the fluid in duct 22. With mouth 48 closed, side walls 41 and 42 function as an effective barrier preventing the entrance of foreign liquid, solid materials, bacteria, viruses, and like material into duct 22 contaminating teat 21 and udder 20 and milk therein.

The entire dilator, including body 27, tubular member 28, flange 36, neck 37, and one-way valve 39, is of a one-piece construction. The entire dilator 26 may be made of a flexible plastic, as polyethylene, silicone, and like rubber materials. The tubular member 28 can be a seamless silicone tubing, such as Silastic tubing sold by the Dow-Corning Corporation, of Midland, Mich. Silastic and like silicone materials are elastic and biologically inert. They do not react with the fluids in the teat duct 22 nor support bacterial growth. Other characteristics of silicone materials are hereinafter described.

Referring to FIGS. 7-12, there is shown a modification of the teat dilator of the invention indicated generally at 126. Dilator 126 is used with the mammary system of a mammal, such as a dairy cow, having an udder 120 and one or more downwardly directed teats 121. Teat 121 has a longitudinal teat duct or cistern 122 in communication with udder cisterns and a duct outlet or streak canal 123 at the terminal end of the teat. Outlet 123 is normally closed with an annular sphincter muscle 124.

Dilator 126 has a tubular body 127 integral with an elongated linear tubular member or finger 128. Body 127 and tubular member 128 have a longitudinal passage 129 for carrying fluid from teat duct 122 externally of teat 121. Tubular member 128 has an angular forward end or tip 131 having an opening 132 open to passage 129. A plurality of holes 133 located in the tubular member provide flow passages from the teat duct 122 to longitudinal passage 129. Openings 133 are longitudinally spaced along the length of tubular member 128. The outer portions of openings 133 have recessed portions providing shallow pockets to facilitate the flow of fluid through holes 133.

Body 127 has a cylindrical neck 134 having a smooth cylindrical outside surface. Neck 134 is joined to an outwardly directed annular flange or head 136 adapted to engage the lower end of teat 121. The upper portion of neck 134 is joined to an annular shoulder 137. Shoulder 137 has a generally cone-shaped outer surface that tapers upwardly and inwardly toward tubular member 129. The cone-shaped outer surface of shoulder 137 facilitates the insertion of shoulder 137 through teat opening 123. Flange 136 and shoulder 137 form with neck 134 an annular groove 138 for accommodating the teat tissue surrounding sphincter muscle 124. As shown in FIG. 8, sphincter muscle 124 retains the teat tissue in groove 138. Shoulder 137 cooperates with sphincter muscle 124 to retain flange 136 in firm engagement with the lower terminal end of teat 121. This minimizes the entrance of fluids and foreign materials through duct outlet 123 and into teat duct 122 thereby controlling mastitis in dairy cows.

A one-way valve indicated generally at 139 is joined to annular flange 136. Valve 139 projects a short distance downwardly from flange 136. When the dilator 126 is inserted into the teat duct 122, one-way valve 139 is located adjacent the end of the teat 121. This closed location of the one-way valve 139 to the end of the teat positions the valve so that it contacts a minimum amount of external fluids and materials that will contaminate the teat duct and fluid therein and minimizes withdrawal of the dilator from the teat by the animal. As shown in FIG. 9, valve 139 has downwardly and inwardly directed flexible side walls 141 and 142 surrounding a chamber 143. Side walls 141 and 142, when in the closed position, have a generally semi-spherical shape. Chamber 143 open to the bottom of passage 129 receives fluid from passage 129. The lower portions side walls 141 and 142 have flexible lips 146 and 147. Lips 146 and 147 have cooperating faces or portions that form a mouth 148. As shown in FIG. 12, mouth 148 is a slit in the lower section of side walls 141 and 142. The flexible side walls 141 and 142 and lips 146 and 147 are elastic so that the mouth 148 can open, as shown in broken lines, and close, as shown in full line. Mouth 148 opens in response to an increase in pressure of the fluid in duct 122 which is transferred through passage 129 to chamber 148 to side walls 141 and 142. When the pressure of the fluid in chamber 143 is reduced, the side walls 141 and 142 return to their normally closed position due to the elastic memory of the material of the side walls. Dilator 126 is a one-piece construction made of a flexible elastic material, such as plastic and like rubber materials. The plastic can be polyethylene or a silicone, such as the Silastic silicone material and like rubber materials. Preferably, the tubular member 128 is a Silastic silicone made by the Dow-Corning Corporation, of Midland, Mich. The silicone material of the dilator is non-reactive to the teat tissue and fluids in the teat. It contains no plasticizer or additives that can leach out into the body tissue. The material is soft and pliable so as to have a minimum of tissue irritation and does not support bacterial growth. Silicone type material will not harden, oxidize, or otherwise deteriorate during prolonged storage. The material also has non-tissue adhering characteristics allowing it to be quickly and easily removed from the teat 121.

The length of the teats and teat ducts of milk cows vary. It is desirable to provide a dilator that does not extend into the milk cistern. Referring to FIG. 13, there is shown dilator 126. Tubular member 128 is bias cut along cut line 151. The cut line 151 is at an angle relative to the longitudinal length of tubular member 128 so as to facilitate the insertion of the tubular member 128 through the duct outlet 123 and into teat duct 122. The bias cut may be 45 degrees relative to the longitudinal axis of tubular member 128. Other angles can be used. A conventional scissors or knife can be used to cut the tubular member 128 to the desired length to fit the teat and duct length. Tubular member 128 is cut about 1 to 2 cm shorter than the length of the teat. When the dilator is used with a long teat, the tubular member 128 is not shortened. The tip of the tubular member can be cut on a bias to facilitate insertion into the teat duct.

An inserter or probe indicated generally at 152 in FIGS. 15 and 16 is used to facilitate the insertion of the dilator 126 into teat 121. The probe 152 has an elongated cylindrical rod 153 terminating in a blunt or rounded forward end 154. Rod 153 is relatively rigid and of a size to fit into passage 129. Rod 153 serves as a rigid carrier for the flexible tubular member 128. A circular member or disc 156 is joined to the lower end of rod 153. A flat triangular-shaped finger gripping member 157 is secured to the bottom of disc 156. The entire probe 152 can be a one-piece plastic or metal. Other types of materials can be used to make probe 152.

Referring to FIG. 15, dilator 126 is located on rod 153 with the one-way valve 139 engaging disc 156. Rod 153 extends through mouth 158 and through dilator passage 129. The forward end of rod 153 extends longitudinally beyond dilator end 131 and is of a length to facilitate the different lengths of tubular members 128.

Referring to FIG. 16, the dilator assembled on the inserter 152 is moved up through duct outlet 123 in the direction of the arrow 158 to locate tubular member 128 in teat duct 122. Dilator 126 is moved upwardly until flange 136 on the upper end of the one-way valve 139 is in firm engagement with the bottom end of teat 121. A slight rotation of inserter 152 facilitates movement of the tubular member 128 and shoulder 137 through to duct outlet 123. Shoulder 137 moves through outlet duct 123 and over the sphincter muscle 124 so that the sphincter muscle holds the teat tissue in firm engagement with neck 134. When the dilator 126 is in its full in or inserted position, as shown in FIG. 17, inserter 152 is pulled in a downward direction, as indicated by arrow 159, and removed from tubular member 128 and one-way valve 139. The flexible side walls 141 and 142 and lips 146 and 147 of the one-way valve return to their normal closed position to prevent the exterior material and fluids from moving through dilator 124 into teat duct 122.

In use, inserter 152 is used in the method of placing the dilator 126 in the inserted position in the teat. The size and length of the teats of dairy cattle vary with the breed and age of the cattle. Dilators of varying lengths are used with the different length teats. When a dilator 126 is used with a relatively short teat, the forward end of the tubular member 128 is initially cut off to shorten the tubular member 128 to a length that is slightly shorter than the length of the teat. Preferably, the tubular member 128 is 1 or 2 cm shorter than the length of the teat duct, so that the forward end or tip of the tubular member 128 does not extend into the milk cistern of the udder. The tubular member 128 is cut along a bias line providing the tubular member 128 with side tapered edges which facilitate the movement of the tubular member 128 through the teat outlet 123 and up into the that canal 122. When the dilator 126 is used with a long teat, the tubular member 128 is not shortened.

The dilator 126 is then mounted on elongated rod 153 of inserter 152. The rod 153 is moved through the slit mouth 148 and up through passage 129 in body 127 and tubular member 128. The forward end of rod 153 projects through the inlet opening 131 of the tubular member 128. The mouth 148 can be initially opened by squeezing the side walls 141 and 142 in the longitudinal direction of the slit mouth 148. The rod 153 can then be slipped through the open mouth and into passage 129. Rod 153 is moved up through the tubular member 128 until the one-way valve 139 engages the top of disc 156. Inserter 152 carrying dilator 126 is ready for insertion into the teat 121.

The dilator 126 and inserter 152 can be washed with water or a disinfecting solution. The solution of liquids will serve as lubricant to ease the insertion of rod 153 and tubular member 128 and body 126 through the duct outlet 123 and into the teat duct 122. Other types of lubricants, as petroleum jelly, can be used with dilator 126 and inserter 152 to ease insertion into the teat duct.

The inserter 152 and dilator 126 is longitudinally moved up through duct outlet 123. The sphincter muscle 124 expands as shoulder 137 moves past the muscle. The inserter 152 and dilator 126 can be rotated during longitudinal movement thereof through the duct outlet 123 into the duct 122 of the teat. When the shoulder 137 moves above sphincter muscle 124, the muscle contracts firmly around cylindrical neck 134. The annular flange 136 is located in firm engagement with the bottom of the teat 121 when the dilator is full in or the inserted position. This locates the one-way valve in close proximity to the end of teat 121. As shown in FIG. 17, the inserter 152 is withdrawn from the dilator 126 by pulling the inserter 152 in the downward direction. The inverted dilator 126 can be held so that it is not withdrawn from the teat 122 with the inserter 152.

Referring to FIGS. 18–21 there is shown a modification of the teat dilator of the invention indicated generally at 226. Dilator 226 is used with the mammary system of a mammal, such as a dairy cow, having an udder and one or more downwardly directed teats 221. Teat 221 has a longitudinal teat duct or cistern 222 in communication with udder cisterns and a duct outlet or streak canal 223 at the terminal end of the teat 221. Outlet 223 is normally closed with an annular sphincter muscle 224.

Dilator 126 has an elongated tubular body 227 having a generally longitudinal passage 229 for carrying fluid from teat duct 222 externally of teat 221. The longitudinal passage may alternatively include a tapered tip 31 as shown in the embodiment of FIG. 3, and may also include small stepped variations in diameter (not shown) to facilitate insertion of the dilator 226 into the teat 221. Tubular body 227 has an opening 232 open to passage 229. Upper holes 233 and lower holes 234 located in the tubular body 227 provide flow passages from the teat duct 222 to longitudinal passage 229. Upper holes 233 are positioned on either side of the tubular body 227 immediately above an upper washer-like ring 230. Lower holes 234 are positioned on either side of the tubular body immediately above a lower washer-like ring 231. These rings 230 and 231 are flexible, as shown in FIG. 20, and assist in maintaining the dilator 226 in the teat 221, and promote draining of fluid through the holes 233 and 234 into the longitudinal passage 229 of the dilator 226. The outer portions of the upper holes 233 and the lower holes 234 have recessed portions providing shallow pockets to facilitate the flow of fluid through the upper holes 233 and lower holes 234.

The tubular body 227 has a cylindrical neck 241 having a smooth cylindrical outside surface. Neck 241 is joined to an outwardly directed annular flange or head 236 adapted to engage the lower end of teat 221. A smaller flange 237 is located adjacent and above the flange 236. The upper portion of neck 241 is joined to the lower ring 231. The neck 241 has a generally cone-shaped outer surface that tapers upwardly and inwardly toward the neck 241. Flange 236, flange 237, and ring 231 form with neck 241 an annular groove 238 for accommodating the teat tissue surrounding sphincter muscle 224. As shown in FIG. 20, sphincter muscle 224 retains the teat tissue in groove 238. Lower ring 231 cooperates with sphincter muscle 224 to retain flange 236 in firm engagement with the lower terminal end of teat 221. This minimizes the entrance of fluids and foreign materials through duct outlet 223 and into teat duct 222 thereby controlling mastitis in dairy cows.

A one-way valve indicated generally at 239 is joined to annular flange 236. Valve 239 projects a short distance downwardly from flange 236. When the dilator 226 is inserted into the teat duct 222, one-way valve 239 is located adjacent the end of the teat 221. This close location of the one-way valve 239 to the end of the teat 221 positions the valve so that it contacts a minimum amount of external fluids and materials that will contaminate the teat duct and fluid therein and minimizes withdrawal of the dilator 226 from the teat 221 by the animal. As shown in FIGS. 20 and 21, valve 239 has downwardly and inwardly directed flexible side walls 240 and 242 surrounding a chamber 243, which is the same diameter as the longitudinal passage 229. Side walls 240 and 242, when in the closed position, have a generally semi-sperical shape. Chamber 243 open to the bottom of passage 229 receives fluid from passage 229. The lower portions of side walls 240 and 242 have flexible lips 246 and 247. Lips 246 and 247 have cooperating faces or portions that form a mouth 248. As shown in FIGS. 20 and 21, mouth 248 is a slit in the lower section of side walls 240 and 242. The flexible side walls 240 and 242 and lips 246 and 247 are elastic so that the mouth 248 can open for the passage of fluid therethrough, as shown in FIG. 21, and close, as shown in FIG. 20. Mouth 248 opens in response to an increase in pressure of the fluid in duct 222 which is transferred through passage 229 to chamber 248 to side walls 240 and 242. When the pressure of the fluid in chamber 243 is reduced, the side walls 240 and 242 return to their normally closed position due to the elastic memory of the material of the side walls.

Dilator 226 is a one-piece construction made of a flexible elastic material, such as plastic and like rubber materials. The plastic can be polyethylene or a silicone, such as the Silastic silicone material and like rubber materials. The inserter 152 shown in FIG. 14, or a similar rigid inserter, can be used with the dilator 226.

Preferably, the tubular member 228 is a Silastic silicone made by the Dow-Corning Corporation, of Midland, Mich. The silicone material of the dilator 226 is non-reactive to the teat tissue and fluids in the teat. It contains no plasticizer or additives that can leach out into the body tissue. The material is soft and pliable so as to have a minimum of tissue irritation and does not support bacterial growth. Silicone type material will not harden, oxidize, or otherwise deteriorate during prolonged storage. The material also has non-tissue adhering characteristics allowing it to be quickly and easily removed from the teat 221.

Dispensers for injecting medicinal compounds into the teat and udder can be used with dilators 26, 126 and 226. The one-way valve with its flexible side walls and lips allows the dispensing probes to be inserted up into the longitudinal passage of the tubular members so that the medicinal compounds can be introduced into the teat duct and udder cisterns.

While there has been shown and described the preferred embodiments of the teat dilator of the invention and the method of inserting the dilator into the teat of a dairy cow, it is understood that changes in the use, materials, structure, arrangement of structure, size and length of the dilators may be made by those skilled in the art without departing from the invention. The invention is defined in the following claims.

The embodiments of the invention in which an exclusive property or privilege is claimed are defined as follows:

1. A dilator for the teat of a female mammal, said teat having a longitudinal duct in communication with a duct outlet in the end of the teat comprising: body means of soft flexible material having a passage adapted to be positioned in the duct outlet to allow fluid to flow through the end of the teat, annular flange means on said body means engageable with the end of the teat when the means secured to the body means is inserted in the duct, at least one ring means on said body means positioned above said annular flange means forming therebetween a channel for accommodating a part of the lower end of the teat when the body means is located in the teat duct, and one-way valve means mounted on said annular flange means for allowing fluid to flow out of the duct through said passage of the body means to discharge the fluid externally of the teat, said one-way valve means having at least a pair of flexible side walls surrounding a valve chamber open to said passage of the body means, said side walls projecting from the body means and extended toward each other, said side walls having cooperating lips surrounding a normally closed mouth to restrict entrance of external foreign substances into the passage of the body means and the duct of said teat.

2. The dilator of claim 1 wherein said ring means includes an upper ring and a lower ring, and said body means includes a pair of opposed upper holes located above said upper ring and a pair of opposed lower holes located above said lower ring.

3. The dilator of claim 2 wherein: said one-way valve means has at least one elongated slit forming the mouth.

4. The dilator of claim 2 wherein: said flexible side walls of the one-way valve means are integral with said annular flange means.

5. The dilator of claim 2 including: a soft, flexible tubular member secured to the body means adapted to be located in the teat duct of the teat, said tubular member having at least one opening allowing milk to flow into the tubular member.

6. A dilator for the teat of a female mammal, said teat having a longitudinal duct in communication with a duct outlet in the end of the teat comprising: body means having a passage adapted to be positioned in the duct outlet to allow fluid to flow through the end of the teat, an elongated tubular member secured to said body means and extended longitudinally thereof adapted to be inserted into the duct outlet in the end of the teat, said tubular member being a soft flexible plastic having a longitudinal passage connected to the passage in the body and a plurality of holes to facilitate flow of fluid from the duct into the longitudinal passage and to the passage of the body means, flange means on said body, said flange means having an annular surface engageable with the end of the teat when the tubular member is inserted into the duct of the teat, and one-way valve means mounted on said flange means for allowing fluid to flow out of the duct through said passage of the body means and discharge the fluid externally of the teat, said one-way valve means having at least a pair of flexible side walls surrounding a valve chamber open to said passage of the body means, said side walls projecting from the body means and extended toward each other, said side walls having cooperating lips surrounding a normally closed mouth to restrict entrance of external foreign substances into the passage of the body means and the duct of the teat.

7. The dilator of claim 6 wherein: said body has a cylindrical outer surface locatable in the duct outlet when the tubular member is located in the duct.

8. The dilator of claim 7 wherein: said flange means is secured to a lower portion of said body means, and an outwardly directed shoulder on an upper portion of the body means, said cylindrical outer surface being located between said flange means and shoulder.

9. The dilator of claim 8 wherein: said shoulder has a forwardly and inwardly tapering outside surface.

10. The dilator of claim 6 wherein: said one-way valve means has at least one elongated slit forming the mouth.

11. The dilator of claim 6 wherein: said flexible side walls of the one-way valve means are integral with said flange means.

12. The dilator of claim 6 including: an outwardly directed shoulder spaced from said flange means and forming therewith a channel for accommodating a part of the lower end of the teat when the tubular member is located in the teat duct.

13. The dilator of claim 12 wherein: said shoulder has a forwardly and inwardly tapering outside surface.

14. The dilator of claim 12 wherein: said one-way valve means has an elongated slit forming the mouth.

15. A dilator for the teat of a female mammal, said teat having a longitudinal duct in communication with a duct outlet in the end of the teat comprising: body means having a passage adapted to be positioned in the duct outlet to allow fluid to flow through the end of the teat, an elongated flexible soft plastic tube secured to said body means adapted to be inserted into the duct through the duct outlet in the end of the teat to facilitate the flow of fluid in the duct to the passage of the body means, said tube having a plurality of openings to allow milk to flow into the tube, annular flange means on said body means engageable with the end of the teat when the tube secured to the body means is inserted in the duct, and one-way valve means mounted on said annular flange means for allowing fluid to flow out of the duct through said tube end passage of the body means and discharge the fluid externally of the teat, said one-way valve means having at least a pair of flexible side walls surrounding a valve chamber open to said passage of the body means, said side walls projecting from the body means and extended toward each other, said side walls having cooperating lips surrounding a normally closed mouth to restrict entrance of external foreign substances into the passage of the body means and the duct of said teat.

16. The dilator of claim 15 wherein: said one-way valve means has at least one elongated slit forming the mouth.

17. The dilator of claim 15 wherein: said flexible side walls of the one-way valve means are integral with said annular flange means.

18. The dilator of claim 15 including: an annular neck and an outwardly directed shoulder on said body means spaced from said flange means and forming therewith a channel for accommodating a part of the lower end of the teat when the tubular member is located in the teat duct.

19. The dilator of claim 18 wherein: said shoulder has a forwardly and inwardly tapering outside surface.

20. The dilator of claim 18 wherein: said one-way valve means has an elongated slit forming the mouth.

21. The dilator of claim 20 wherein: said flexible side walls of the one-way valve means are integral with said flange means.

* * * * *

UNITED STATES PATENT AND TRADEMARK OFFICE
CERTIFICATE OF CORRECTION

PATENT NO. : 4,385,633

DATED : May 31, 1983

INVENTOR(S) : Francis W. Child

It is certified that error appears in the above-identified patent and that said Letters Patent is hereby corrected as shown below:

On the title page, the inventor's address "Eagle Bend, Minn." should be --Cody, Wyoming--.

Column 3, line 7, "enlarged" should be --elongated--.

Column 6, line 11, "158" should be --148--.

Signed and Sealed this

Fifth Day of June 1984

[SEAL]

Attest:

GERALD J. MOSSINGHOFF

Attesting Officer         Commissioner of Patents and Trademarks